United States Patent [19]
Furuya

[11] Patent Number: 5,257,087
[45] Date of Patent: Oct. 26, 1993

[54] METHOD AND APPARATUS FOR MEASURING PARTICLES IN A FLUID

[75] Inventor: Yoshiyuki Furuya, Tokyo, Japan

[73] Assignee: Kowa Company Ltd., Japan

[21] Appl. No.: 701,185

[22] Filed: May 16, 1991

[30] Foreign Application Priority Data

May 21, 1990 [JP] Japan ................... 2-129123

[51] Int. Cl.$^5$ .................... G01N 15/02; G01N 15/14
[52] U.S. Cl. ................... 356/336; 356/335; 356/337; 356/341; 356/342
[58] Field of Search ............. 356/336, 335, 337, 338, 356/341, 342, 343

[56] References Cited
U.S. PATENT DOCUMENTS

| | | | |
|---|---|---|---|
| 4,021,117 | 5/1987 | Göhde | 356/335 |
| 4,854,705 | 8/1989 | Bachalo | 356/336 |
| 5,037,202 | 8/1991 | Batchelder | 356/336 |
| 5,126,581 | 6/1992 | Furuya | 356/336 |

Primary Examiner—Vincent P. McGraw
Assistant Examiner—Keesee, LaCharles
Attorney, Agent, or Firm—Bruce L. Adams; Van C. Wilks

[57] ABSTRACT

Disclosed is a method and apparatus for measuring particles in a fluid by irradiating the fluid containing the particle with a laser beam and deriving particle characteristics such as diameter and size distribution from the intensity of the light scattered by the particles. Based on the value of the output of a photomultiplier used to detect the scattered light, it is determined whether a particle is a fine particle, which is a particle with a photoelectron pulse count that does not exceed a prescribed value, or a large particle, and these particles are counted separately. Fine particles are processed using photon counting, and large particles are processed by an analog process, in which case the threshold values used to discriminate particles are varied in accordance with pre-stored data on the refractive index of each fluid.

3 Claims, 5 Drawing Sheets

METHOD AND APPARATUS FOR MEASURING PARTICLES IN A FLUID

BACKGROUND OF THE INVENTION

1. Field of the Invention

This invention relates to a method and apparatus for measuring particles in a fluid, and more particularly to a method and apparatus for measuring particle characteristics such as the diameter and size distribution of particles in a fluid, by using a laser beam to irradiate the particle-containing fluid as it flows through a measurement cell, detecting the laser light scattered by the particles in the fluid and determining the characteristics from the intensity of the scattered laser light.

2. Description of the Prior Art

As the density level of large-scale integrated memories and other such semiconductor devices continues to rise, going from 4-megabit to 16-megabit, the high-purity water and chemicals used in the semiconductor fabrication processes have to be of the highest quality, containing no impurities. Controlling fine particles in the pure water and chemicals is particularly important as this has a major effect on LSI yield levels.

One way of measuring fine particles in water and chemicals has been to use a scanning electron microscope. However, using a scanning electron microscope has the drawback of being very costly and lacking real-time capabilities. One widespread solution to this has been to use a particle measurement method comprising irradiating the fluid with a laser beam and determining the particle diameter from the intensity of the laser light scattered by the particles.

The theoretical intensity of the Mie scattering of light from a spherical particle in a fluid can be calculated. It is known that the intensity of light scattered by a particle having a diameter that is smaller than one-tenth the wavelength of the incident laser beam will be proportional to the fifth to sixth power of the particle diameter. It therefore follows that a decrease in the particle diameter is accompanied by a weakening in the intensity of the scattered light, and that to be able to detect such weak light it is necessary to use a detection apparatus that has good signal/noise (S/N) ratio characteristics. Single photon counting is an effective method for detecting weak light.

A conventional apparatus utilizing single photon counting will first be explained with reference to FIG. 5. In FIG. 5, a laser beam from a laser light source 1 passes through a lens 2 which focuses the light onto a particle measurement region 4 of a measurement cell 3. The laser light is scattered by particles which pass through the measurement region 4. The light thus scattered by the particles is condensed by a lens 5 to form an image at a slit 6. The scattered light passes through the slit 6 and impinges on a photomultiplier (PM) 7 whereby the scattered light is converted to electrical signals and output as photoelectron pulses. These output signals are amplified by a preamplifier 8 and are then converted to digital signals by a peak discriminator (DISC) 9 and a pulse shaper 10, and the digital signals output from the pulse shaper 10 are then counted by a pulse counter 11 and the count value is stored in a memory 12 in the form of a time series. The time series data stored in the memory 12 is then analyzed by a processor 13, which uses the intensity values of the scattered light to calculate particle diameter and particle concentration.

Use of the single photon counting method makes it possible to eliminate the dark current and fluctuations in the multiplication factor that are causes of noise in the photomultiplier, providing a three- to five-fold improvement in the S/N ratio compared with the usual analog method. With the single photon counting method, the intensity of the scattered light can be measured by counting the number of photoelectron pulses per unit time interval.

However, the number of photoelectron pulses that can be counted per unit time period is limited by the pulse width and the frequency characteristics of the electrical system constituting the photon counters. Photons reaching the photoelectric surface of the photomultiplier cause electrons to be emitted from the same surface by the photoelectric effect. The electrons emitted from the photoelectric surface are multiplied in number within the photomultiplier by a factor of approximately $10^6$. Because of variations in the scanning distance that arise in the course of the electron multiplication in the photomultiplier, each pulse that is output corresponding to the emission of an electron from the photoelectric surface is given a time width.

In the case of side-on type photomultipliers, this time width is usually in the order of 2 ns. Therefore, the emission from the photoelectric surface of electrons at intervals shorter than 2 ns will cause superposing of the photoelectron pulses output by the photomultiplier and make it impossible to count single photons. Even if electrons are emitted at longer intervals than the time width of the photoelectron pulses, the upper count per unit time period is limited by the frequency characteristics of the electrical system constituting the photon counters.

Thus, the three- to five-fold improvement in the S/N ratio compared with analog methods enables smaller particles to be measured with the single photon counting method, with this method the dynamic range is limited by the time width of the photoelectron pulses and the frequency characteristics of the electrical system of the photon counters to a count rate of about $10^8$ per second and cannot be used to accurately determine the intensity of high-intensity scattered light from large particles.

In accordance with Mie's scattering theory, the intensity of light scattered by particles in a fluid will also depend on the refractive index of the fluid. Thus, if each fluid (medium) containing the particles has a different refractive index, the intensity of light scattered by particles having the same diameter or refractive index will vary depending on the fluid. As such, in determining particle diameter it is also necessary to take into account the refractive index of the fluid containing the particles which are to be measured.

SUMMARY OF THE INVENTION

An object of the present invention is to solve these drawbacks of the prior art and to provide a method and apparatus for measuring particles in a fluid which enable various characteristics of particles in a fluid to be determined with good accuracy regardless of the size of the particles or of the refractive index of the fluid containing the particles.

According to the present invention there is provided a method for measuring particles in a fluid flowing in a measurement cell by irradiating the fluid containing the particles with a laser beam, detecting the laser light scattered by the particles and using the intensity of the scattered light to derive the diameter and size distribution of the particles, the method comprising determining from the value of a signal output by a photomultiplier that detects scattered light from particles whether or not a particle is a fine particle that does not exceed a prescribed value, wherein particle diameter and size distribution are derived by using single photon counting when particles are determined as being fine particles with a photoelectron pulse count that does not exceed a prescribed value and by using analog processing when particles exceed the prescribed value, and when analog processing of the signals is applied particle diameter is determined by applying a threshold value which is varied in accordance with the refractive index of the fluid containing the particles.

The present invention also comprises an apparatus for measuring particles in a fluid flowing in a measurement cell by irradiating the fluid containing the particles with a laser beam, detecting the laser light scattered by the particles and using the intensity of the scattered light to derive the diameter and size distribution of the particles, the apparatus comprising a photomultiplier for detecting light scattered by particles, first counting means for counting photoelectron pulses corresponding to signals output by the photomultiplier, pulse height comparison means for comparing the pulse height of amplified signals from the photomultiplier with a prescribed threshold value, second counting means for counting signals having pulse height values which exceed the prescribed threshold value, discrimination means for discriminating whether or not measured particles are fine particles with a photoelectron pulse count that does not exceed a prescribed value, processor means for calculating particle diameter and size distribution based on signals from the first and second counting means, and means for inputting the refractive indexes of fluids, wherein the calculating processor means derives the diameter and size distribution of particles based on signal counts from the first counting means which counts particles determined as being fine particles giving rise to a photoelectron pulse count that does not exceed a prescribed value, and signal counts from the second counting means which counts particles determined as being larger particles giving rise to a photoelectron pulse count that exceeds the prescribed value, and in which the threshold value of the pulse height comparison means is changed in accordance with the input refractive index of the fluid.

Using this arrangement to determine particle diameter from the intensity of the light scattered by particles enables the threshold value used to determine particle diameter based on the intensity of the light scattered by particles, which depends on the refractive index of the fluid concerned, to be set for the refractive index of each fluid, providing more accurate determination of particle size.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Embodiments of the invention will now be described in detail with reference to the drawings.

Figure 1:
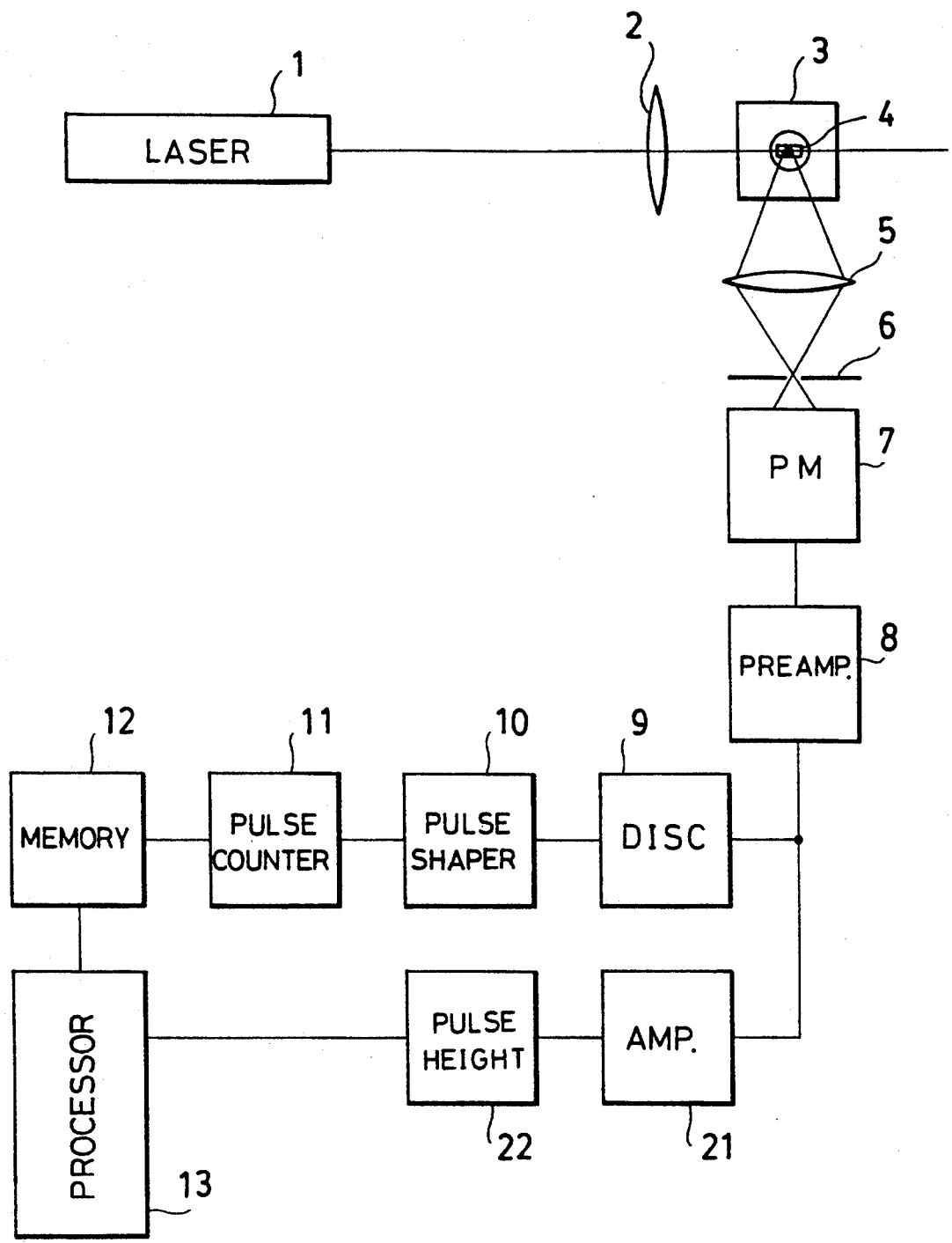
FIG. 1 is a block diagram illustrating the structure of the apparatus according to a first embodiment of the present invention.
Figure 5:
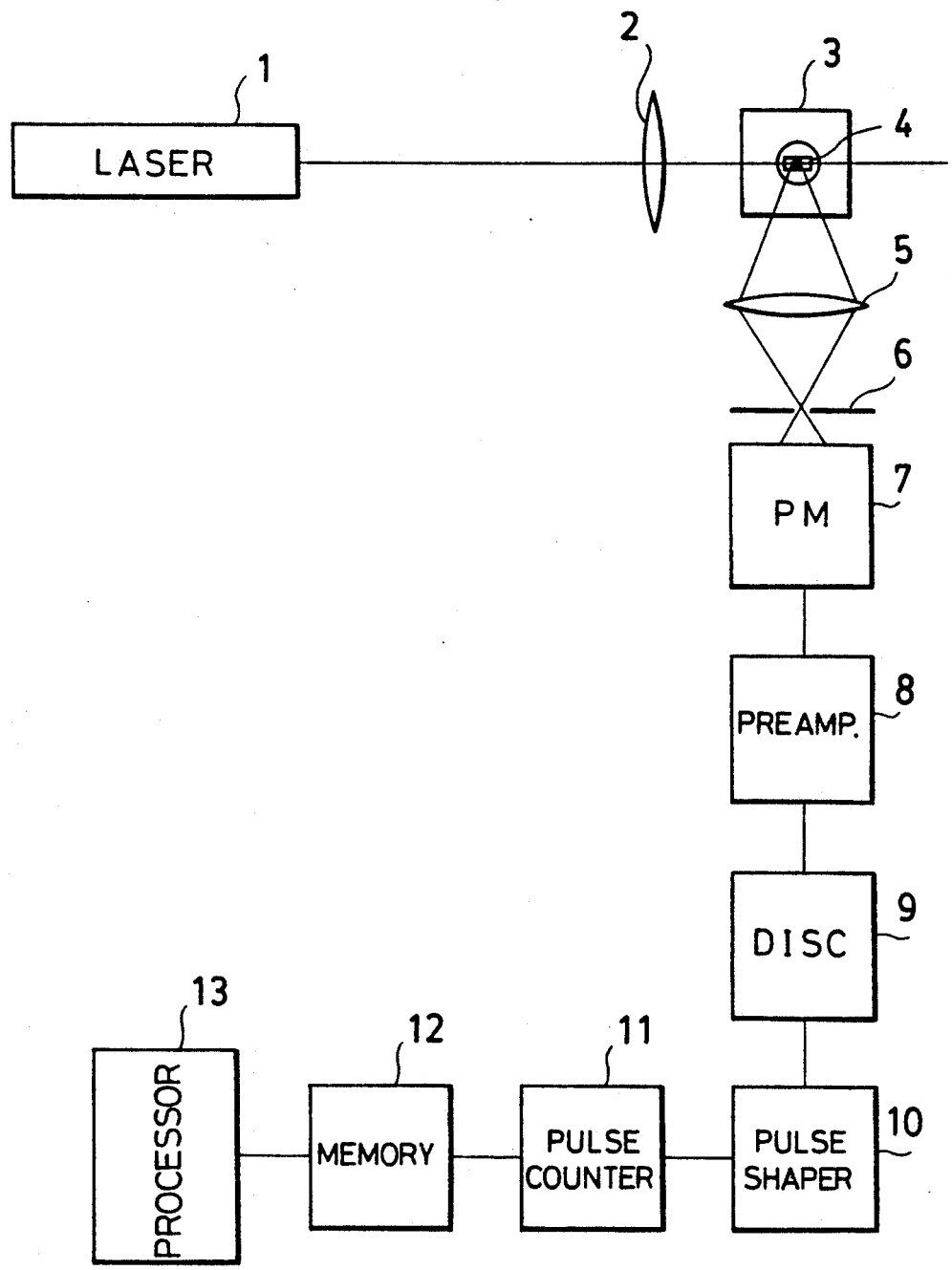
FIG. 5 is a block diagram illustrating the structure of a prior art apparatus.

The structure of a first embodiment of the apparatus according to the invention is shown in FIG. 1. Components thereof that are identical with those in FIG. 5 are denoted by like reference numerals and will not be explained again here.

With reference to FIG. 1, signals received from a photomultiplier 7 and amplified by a preamplifier 8 are split, with one side being subjected to signal processing by a conventional single photon counting method. An amplifier 21 and an analog pulse height analyzer 22 are provided for subjecting the other side to analog processing when the intensity of the scattered light is too high for photon counting. The preamplifier 8 should have frequency characteristics that match the time width of the photoelectron pulses (about $10^{-9}$ seconds), but the amplifier 21 only needs to have a frequency characteristic that can match the time period it takes the laser beam to sweep a particle (about $10^{-3}$ seconds). The method used for signal processing by single photon counting is the same as the conventional one. The analog pulse height of signals amplified by the amplifier 21 and each having the time width of the passage of a particle through the laser beam is analyzed by the analog pulse height analyzer 22 and the particle size distribution is derived by a processor 13.

The processor 13 determines whether or not the signal pulse count value counted by a pulse counter 11 is equal to or below a prescribed value. If the count value is equal to or below the prescribed value, the measured particle is determined as being a fine particle and the single photon counting procedure is used to calculate particle diameter and size distribution. If the count value exceeds the prescribed value, particle diameter and size distribution are calculated using an analog method based on the signal output of the analog pulse height analyzer 22.

The operation of the apparatus shown in FIG. 1 will now be explained. A laser light source 1 emits a light beam having a space intensity distribution such as the one illustrated by FIG. 2a. This laser beam irradiates particles that flow through the measurement zone 4 of a measurement cell 3. In the TEM00 mode the space intensity distribution of the laser light is Gaussian. When a particle of a given velocity passes through such a beam, the time envelope of the scattered light intensity from the particle will reflect the space intensity distribution of the laser beam.

Figure 2:
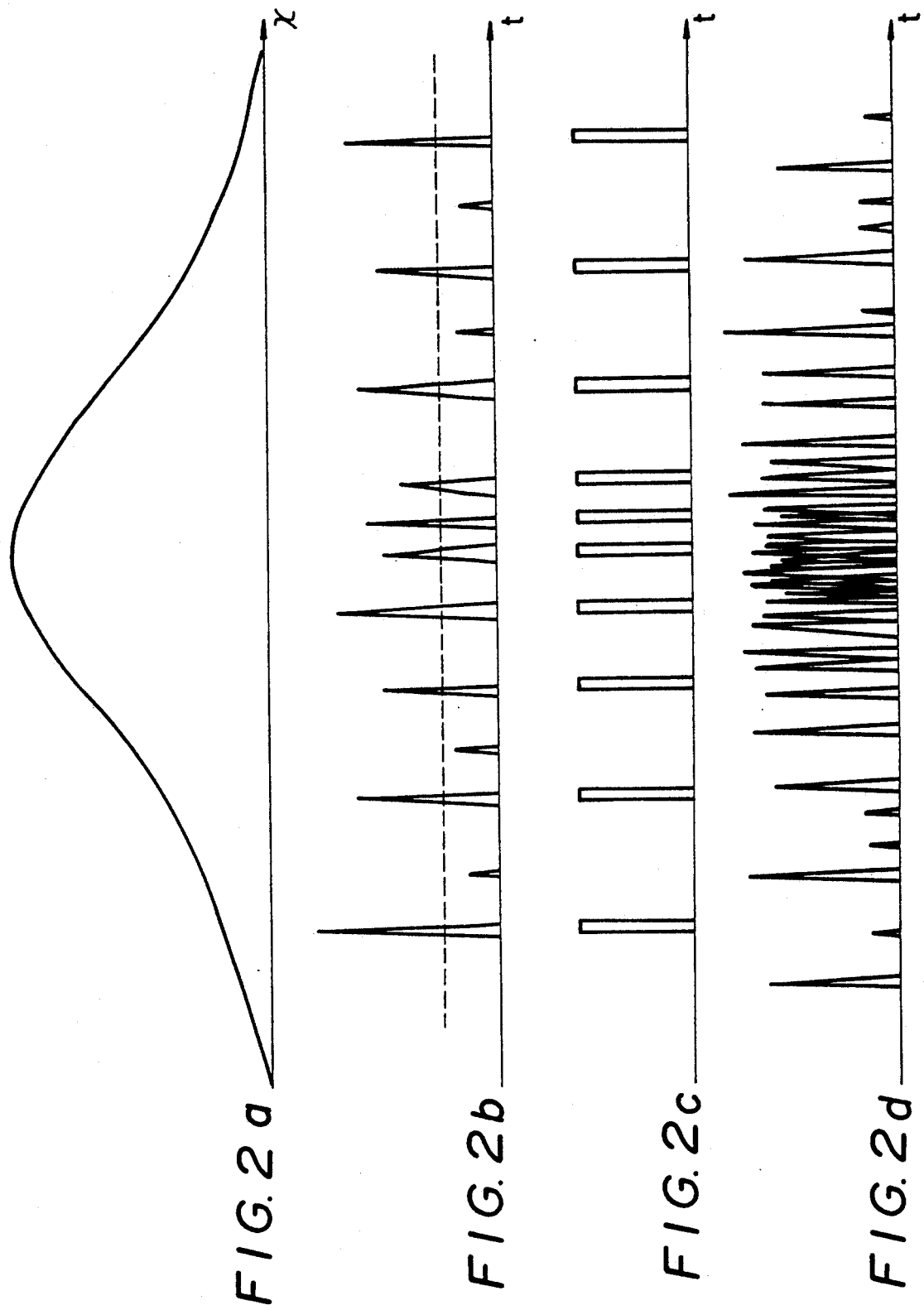
FIGS. 2a to 2d are signal waveform diagrams for explaining the operation of the apparatus illustrated in FIG. 1.

FIG. 2b shows time-based changes in a signal output by the photomultiplier 7 when a fine particle passes through the laser beam. Because of the weak nature of the scattered light from the fine particle, the photoelectron pulses become dispersed, with no overlapping.

FIG. 2c shows the digitized signal produced by a pulse height discriminator 9 from a signal with an amplitude exceeding the level represented in FIG. 2b by the broken line. Digitizing makes it possible to remove dark current components with a smaller amplitude than the broken-line level and also eliminates fluctuation in the multiplication factor of the photomultiplier. Digital pulses that have been pulse height discriminated are counted in the pulse counter 11 and stored as time-series measurement data in a memory 12.

FIG. 2d shows time-based changes in a signal output by the photomultiplier 7 when a large particle passes through the laser beam. The high intensity of scattered light produced by large particles, especially when the particle passes through the center of the beam, causes superposing of photoelectron pulses. This kind of photoelectron pulse increases the count value by the pulse counter 11, and the processor 13 determines whether or not this pulse count value of the pulse counter 11 is equal to or below the prescribed value. If the pulse count value does not exceed the prescribed value, the processor 13 determines the measured particle is a fine particle and the single photon counting procedure is used to calculate particle diameter and size distribution based on the data stored in the memory 12.

If the pulse count value output by the pulse counter 11 exceeds the prescribed value, meaning that the measured particles are large ones such as the ones that produced the waveform shown in FIG. 2d, the particle diameter and size distribution are derived by applying a prescribed operation expression using an analog method based on the signal output of the analog pulse height analyzer 22. The processor 13 incorporates comparator functions with the threshold values corresponding to the particle diameters, and the size distribution is derived based on the count values of signals having pulse height values that exceed those threshold values.

In the embodiment described above, a processor is used to determine whether photoelectron pulse count values do or do not exceed the prescribed values, but a determination circuit or discriminator that is separate from the processor may be used for this purpose.

As mentioned above, as in accordance with Mie's scattering theory the intensity of light scattered by particles in a fluid (medium) also depends on the refractive index of the fluid, if each fluid containing the particles has a different refractive index the intensity of light scattered by particles having the same diameter or refractive index will vary from fluid to fluid. It therefore follows that particle diameter determination based on fixed threshold values will contain errors.

Figure 3:
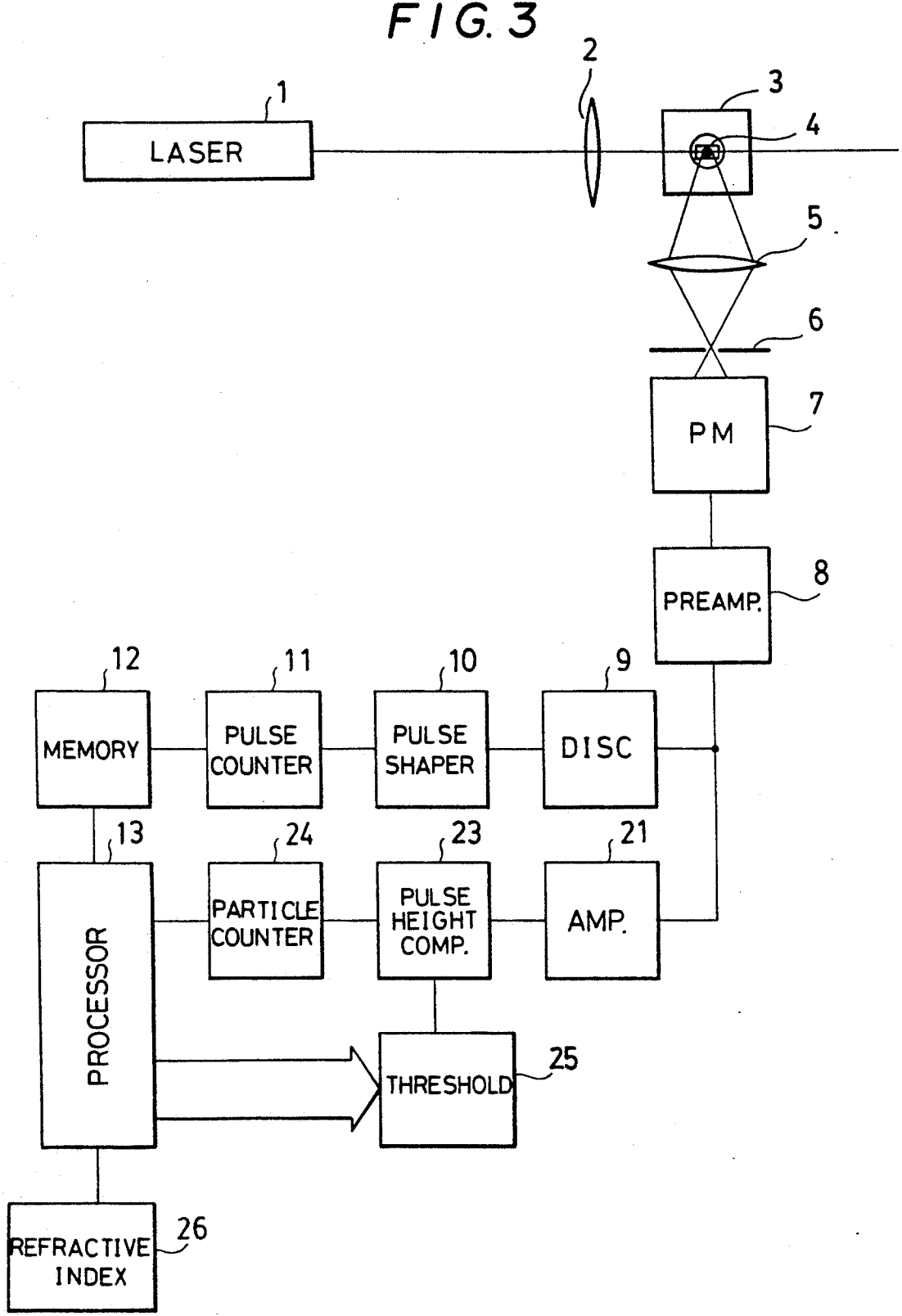
FIG. 3 is a block diagram of another embodiment of the apparatus according to the present invention.

A further embodiment of the invention for solving this problem is illustrated in FIG. 3. The apparatus for applying signal processing by the photon counting method is the same as the apparatus of FIG. 1 and further explanation thereof is omitted here. Concerning the analog signal processing side, up to the amplifier 21 the arrangement is the same as that of FIG. 1, but there is an analog pulse height comparator 23 instead of the analog pulse height analyzer 22, and in addition to the components shown in FIG. 1 there are a particle counter 24, a threshold value voltage setter 25 and a refractive index input means 26. In the arrangement illustrated in FIG. 1 the analog pulse height comparator 23 and particle counter 24 are provided inside the processor 13, whereas in the embodiment shown in FIG. 3 these components are provided outside the processor 13.

The refractive index of the particular fluid that is input into the refractive index input means 26 is read by the processor 13 which then calculates the scattered light intensity of particles for the refractive index of the fluid. Based on the scattered light intensity ratio, the processor 13 then sends signal data to the threshold value voltage setter 25 which sets the threshold value voltage accordingly. When the scattered light intensity is recognized as indicating the scattered light is from a particle, based on the threshold value voltage data signal transmitted from the threshold value voltage setter 25 to the analog pulse height comparator 23 and the scattered light intensity data signal transmitted from the amplifier 21 to the analog pulse height comparator 23, the analog pulse height comparator 23 sends a signal to the particle counter 24, incrementing the particle count. The processor 13 then reads the particle count and calculates the particle size distribution.

Figure 4:
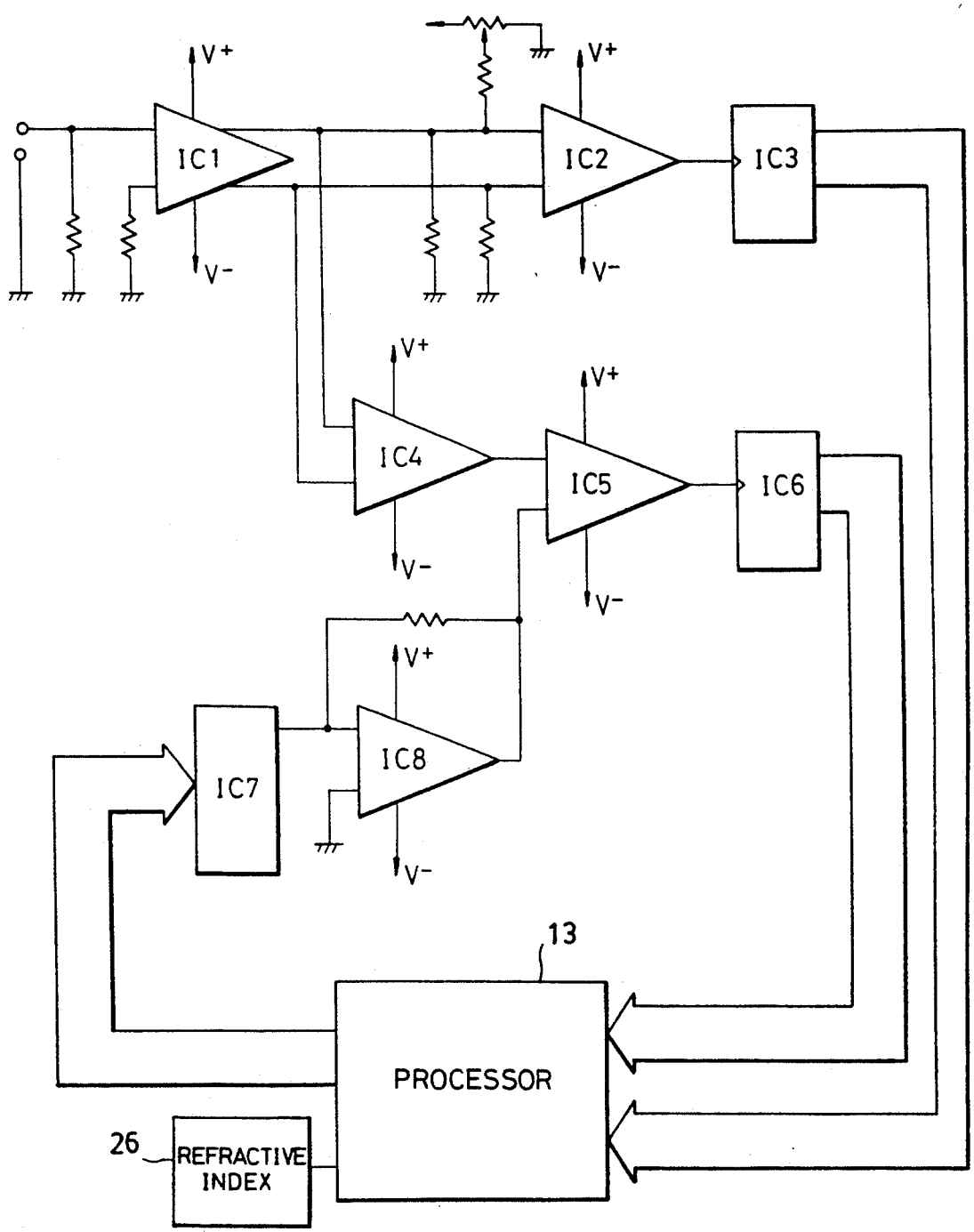
FIG. 4 is a more detailed diagram of the circuit arrangement of the apparatus of FIG. 3.

FIG. 4 shows an example of a circuit arrangement for realizing this embodiment. IC1 is the preamplifier 8 for amplifying the signals from the photomultiplier, and IC2 is the pulse height discriminator 9 for signal processing by the photon counting method. The signal is sent as a digital signal to IC3, which is a digital counter (corresponding to the pulse counter 11 shown in FIG. 1). The IC3 count value is read by processor 13. The signals amplified by IC1 are re-amplified by IC4 (which corresponds to amplifier 21) and sent to IC5 (corresponding to analog pulse height comparator 23) for pulse height comparison.

The refractive index of the particular fluid that is input into the refractive index input means 26 is read by the processor 13 which then sends digital data relating to threshold value voltage to IC7, which is a D/A converter. The D/A converter output is in the usual form of an electric current, which is converted to voltage by IC8, and IC8 outputs a threshold value voltage signal to IC5. If IC5 recognizes that signal data received from IC4 relates to light scattered by a particle, IC5 outputs a digital signal which increments the particle count of digital counter IC6 (which corresponds to particle counter 24), and this particle count value is read by the processor 13 which uses this value to calculate the particle size distribution.

While this embodiment has been described with reference to a single pulse height comparator, multiple pulse height comparators may of course be used to set threshold values for multiple particle determination.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A method for measuring particles in a fluid flowing in a measurement cell by irradiating the fluid containing the particles with a laser beam, detecting the laser light scattered by the particles and using the intensity of the scattered light to derive the diameter and size distribution of the particles, comprising the steps of:

determining from the value of a signal output by a photomultiplier that detects scattered light from particles whether or not a particle is a fine particle that does not exceed a prescribed value;

deriving particle diameter and size distribution by using photon counting when the particles are determined as being fine particles with a photoelectron pulse count that does not exceed a prescribed value, and by using analog processing when the particles are determined as exceeding the prescribed value; and when analog processing of signals is applied, determining particle diameter by applying a threshold value which is varied in accordance with the refractive index of the fluid containing the particles.

2. An apparatus for measuring particles in a fluid flowing in a measurement cell by irradiating the fluid containing the particles with a laser beam, detecting the laster light scattered by the particles and using the intensity of the scattered light to derive the diameter and size distribution of the particles, comprising:

a photomultiplier for detecting light scattered by particles;

first counting means for counting photoelectron pulses corresponding to signals output by the photomultiplier;

analog pulse height comparison means for comparing the pulse height of amplified signals from the photomultiplier with a prescribed threshold value;

second counting means for counting signals having pulse height values which exceed said prescribed threshold value;

discrimination means for discriminating whether or not measured particles are fine particles with a photoelectron pulse count that does not exceed a prescribed value;

processor means for calculating particle diameter and size distribution based on signals from the first and second counting means; and means for inputting to the processor means data corresponding to the refractive indexes of fluids;

wherein the diameter and size distribution of particles are derived by the processor means from signal counts from the first counting means in the case of particles determined as being fine particles giving rise to a photoelectron pulse count that doe snot exceed a prescribed value, and from signal counts from the second counting means in the case of particles determined as being large particles giving rise to a count that exceeds the prescribed value, and the threshold value of the analog pulse height comparison means is changed in accordance with the input refractive index of the fluid.

3. An apparatus as set forth in claim 2, further comprising multiple pulse height comparison means having different threshold values.

* * * * *